United States Patent
Bondesen et al.

(10) Patent No.: US 10,993,988 B2
(45) Date of Patent: May 4, 2021

(54) ANTHELMINTIC COMBINATIONS AND METHODS OF USE THEREOF

(71) Applicant: BOEHRINGER INGELHEIM ANIMAL HEALTH USA INC., Duluth, GA (US)

(72) Inventors: Brenda Bondesen, Atlanta, GA (US); Lance Hammerland

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 634 days.

(21) Appl. No.: 15/089,282

(22) Filed: Apr. 1, 2016

(65) Prior Publication Data

US 2017/0020955 A1    Jan. 26, 2017

Related U.S. Application Data

(60) Provisional application No. 62/142,304, filed on Apr. 2, 2015.

(51) Int. Cl.
| | | |
|---|---|---|
| *A61K 38/15* | (2006.01) | |
| *A61K 31/5377* | (2006.01) | |
| *A61K 31/7048* | (2006.01) | |
| *A61K 9/00* | (2006.01) | |
| *A61K 31/365* | (2006.01) | |
| *A61K 31/4985* | (2006.01) | |
| *A61K 31/55* | (2006.01) | |

(52) U.S. Cl.
CPC ............ *A61K 38/15* (2013.01); *A61K 9/0056* (2013.01); *A61K 31/365* (2013.01); *A61K 31/4985* (2013.01); *A61K 31/5377* (2013.01); *A61K 31/55* (2013.01); *A61K 31/7048* (2013.01); *A61K 2300/00* (2013.01)

(58) Field of Classification Search
CPC .... A61K 38/15; A61K 9/0056; A61K 31/365; A61K 31/4985; A61K 31/5377; A61K 31/55; A61K 31/7048; A61K 2300/00
See application file for complete search history.

(56) References Cited

U.S. PATENT DOCUMENTS

| | | | | |
|---|---|---|---|---|
| 6,159,932 A * | 12/2000 | Mencke | ............... | A61K 38/15 514/4.6 |
| 8,709,440 B2 | 4/2014 | Meijs et al. | | |
| 2008/0200540 A1 * | 8/2008 | Gibson | ............... | C07D 307/81 514/469 |
| 2011/0046072 A1 | 2/2011 | Venkata-Rangarao | | |
| 2011/0263489 A1 | 10/2011 | Aroian et al. | | |
| 2012/0295931 A1 | 11/2012 | Lutz et al. | | |
| 2014/0163056 A1 | 6/2014 | Chassaing et al. | | |

FOREIGN PATENT DOCUMENTS

| | | |
|---|---|---|
| AU | 2010101389 A4 | 1/2011 |
| AU | 2010249226 A1 | 6/2012 |
| JP | 2008247806 A | 10/2008 |
| RU | 2452180 C2 | 6/2012 |

OTHER PUBLICATIONS

Bowman, Parasites & Vectors 2012, 5:138.*
Godel et al., FASEB J. 26, 4650-4661 (2012).*
Parasitology. Mar. 2005;130(Pt 3):343-7, Abstract only provided.*
Bowman, Parasites & Vectors 2012, 5:138 (Year: 2012).*
Harder et al., Intl. Jl. Antimicrob. Agents 22 (2003) 318-331 (Year: 2003).*
Pulaski et al., Parasites and Vectors 2014, 7:494 (Year: 2014).*
Hu et al., PNAS Mar. 30, 2010, vol. 107, No. 3, 5955-5960 (Year: 2010).*
Blagburn, Vet. Parasitology 176 (2011)189-194 (Year: 2011).*
Hsu, Handbook of Veterinary Pharmacology, Wiley Blackwell, 2008, Chapter 16 (Year: 2008).*
Geary et al., Topics in Companion Animal Med. vol. 26, No. 4, Nov. 2011 (Year: 2011).*
Bourguinat et al., Parasites & Vectors 2017, 10(Suppl 2):494 (Year: 2017).*
Bourguinat, Veterinary Parasitology 210 (2015) 167-178 (Year: 2015).*
Web page print-out regarding commercial product PROFENDER for DOGS obtained from the internet Sep. 10, 2020, from the following site/address: https://parasitipedia.net/index.php?option=com_content&view=article&id=2817&Itemid=3139 (Year: 2020).*
Krudewagen, E. M., and Annette Schimmel. "Concomitant simultaneous and consecutive treatment of imidacloprid/moxidectin spot-on with emodepside/praziquantel tablets in adult dogs." Intern. J. Appl. Res. Vet. Med 9.3 (2011): 290-299.
von Samson-Himmelstjerna, G., et al. "Efficacy of two cyclooctadepsipeptides, PF1022A and emodepside, against anthelmintic-resistant nematodes in sheep and cattle." Parasitology 130.3 (2005): 343-347.
Harder, Achim, et al. "Cyclooctadepsipeptides—an anthelmintically active class of compounds exhibiting a novel mode of action." International journal of antimicrobial agents 22.3 (2003): 318-331.
Nwosu, Uzoma, et al. "Efficacy of the cyclooctadepsipeptide PF1022A against Heligmosomoides bakeri in vitro and in vivo." Parasitology 138.9 (2011): 1193-1201.
Blagburn, Byron L., et al. "Efficacy of four commercially available heartworm preventive products against the JYD-34 laboratory strain of *Dirofilaria immitis*." Parasites & vectors 9.1 (2016): 191.

(Continued)

*Primary Examiner* — Larry D Riggs, II
*Assistant Examiner* — Joseph Fischer
(74) *Attorney, Agent, or Firm* — John Ezcurra

(57) ABSTRACT

The present invention relates to a veterinary composition comprising an effective amount of at least one cyclic depsipeptide and at least one macrocyclic lactone; and a pharmaceutically acceptable carrier, for the treatment or prophylaxis of parasitic infection in a mammal wherein the parasite shows resistance to treatment or prophylaxis with the macrocyclic lactone alone.

13 Claims, No Drawings

(56) References Cited

OTHER PUBLICATIONS

Atkins, Clarke E., et al. "Heartworm 'lack of effectiveness' claims in the Mississippi delta: Computerized analysis of owner compliance—2004-2011." Veterinary parasitology 206.1-2 (2014): 106-113.

Blagburn, B., et al. "Evidence of genetic selection following treatment of a heartworm-infected, microfilaremic dog with increasing doses of ivermectin. Chicago, IL, USA: American Association of Veterinary Parasitologists." 58th Annual Meeting. 2013.

Snyder, D. E., et al. "Ivermectin and milbemycin oxime in experimental adult heartworm (*Dirofilaria immitis*) infection of dogs." Journal of veterinary internal medicine 25.1 (2011): 61-64.

Gyles, Carlton. "Heartworm resistance." The Canadian Veterinary Journal 52.12 (2011): 1279.

Geary, Timothy G., Catherine Bourguinat, and Roger K. Prichard. "Evidence for macrocyclic lactone anthelmintic resistance in Dirofilaria immitis," Topics in companion animal medicine 26.4 (2011): 186-192.

Pulaski, Cassan N., et al. "Establishment of macrocyclic lactone resistant Dirofilaria immitis isolates in experimentally infected laboratory dogs." Parasites & vectors 7.1 (2014): 494.

Blagburn, B. L., et al. "Comparative efficacy of four commercially available heartworm preventive products against the MP3 laboratory strain of *Dirofilaria immitis*." Veterinary parasitology 176.2-3 (2011): 189-194.

Dryden, M.W., "Canine Heartworm Update: What we forgot, what we thought we knew and what we need to know," downloaded from https://delawarevalleyacademyvm.org/pdfs/may11/1Canine_Heartworm_2011.pdf.

Bourguinat, Catherine, et al. "Correlation between loss of efficacy of macrocyclic lactone heartworm anthelmintics and P-glycoprotein genotype." Veterinary parasitology 176.4 (2011): 374-381.

Kaplan, Ray M. "Drug resistance in nematodes of veterinary importance: a status report." Trends in parasitology 20.10 (2004): 477-481.

Geary, Timothy G. "Ivermectin 20 years on: maturation of a wonder drug." Trends in parasitology 21.11 (2005): 530-532.

Prichard, R. K. "Is anthelmintic resistance a concern for heartworm control?: what can we learn from the human filariasis control programs?." Veterinary Parasitology 133.2-3 (2005): 243-253.

Bourguinat, Catherine, et al. "Genetic polymorphism in Dirofilaria immitis." Veterinary parasitology 176.4 (2011): 368-373.

Bourguinat, Catherine, et al. "Macrocyclic lactone resistance in Dirofilaria immitis." Veterinary parasitology 181.2-4 (2011): 388-392.

Bourguinat, Catherine, Veterinary Parasitology, 182(2011): 380-381.

* cited by examiner

ANTHELMINTIC COMBINATIONS AND METHODS OF USE THEREOF

RELATED APPLICATIONS/INCORPORATION BY REFERENCE

This application claims the benefit of priority to U.S. provisional application No. 62/142,304 filed Apr. 2, 2015, which is incorporated herein by reference in its entirety.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

FIELD OF THE INVENTION

This invention relates to anthelmintic combinations which comprise at least one macrocyclic lactone and at least one cyclic depsipeptide to treat parasitic resistant worms or helminth infections. This invention also relates to uses of the compounds to make medicaments and treatments comprising the administration of the compounds to mammals in need of the treatments. Moreover this invention relates to pharmaceutical compositions and kits comprising the compounds. This invention also provides for an improved method for eradicating, controlling, and preventing parasite infestation in mammals.

BACKGROUND OF THE INVENTION

Animals, such as mammals and birds, are often susceptible to parasite infestations. These parasites may be ectoparasites, such as insects, and endoparasites such as filariae and worms. Animals and humans also suffer from endoparasitical infections including, for example, helminthiasis which is most frequently caused by a group of parasitic worms described as nematodes or roundworms. These parasites cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

One type of endoparasite which seriously harms mammals is *Dirofilaria immitis*, also known as heartworm. The most common hosts are dogs and cats but other mammals such as ferrets and raccoons may also be infected. Heartworms go throughout several life stages before they become adults infecting the pulmonary artery of the host mammal. The worms require the mosquito as an intermediate stage to complete their life cycles. The period between the initial infection when the dog is bitten by a mosquito and the maturation of the worms into adults living in the heart takes six to seven months in dogs and is known as the "prepatent period". L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years. After mating, female worms release larvae known as microfilariae (or L1) into the circulation. The microfilariae circulate in the bloodstream for as long as two years, waiting for the next stage in their life cycles in the gut of a bloodsucking mosquito. When ingested by a mosquito, the microfilariae undergo a series of molts to the infective third larval stage, and then migrate to the salivary glands of the mosquito, where they wait to infect another host.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of heartworm preventive therapy in dogs has been to stop infection by *Dirofilaria immitis* by killing the stage that is deposited by the mosquito and first enters the dog, the third-stage larva (L3), as well as the young and maturing fourth-stage larva (L4). Macrocyclic lactones (MLs) can be used monthly for uninfected dogs to suppress reproduction in adult worms and remove microfilariae, thereby reducing transmission and gradually causing the attrition of adult worms (*Veterinary Parasitology* 2005 Oct. 24 133(2-3) 197-206).

The macrocyclic lactones (e.g. ivermectin, milbemycin oxime, moxidectin, and selamectin) are the most commonly used chemoprophylaxis agents and are administered at monthly or six-month intervals. These drugs have been effective against *Dirofilaria immitis* third-stage larvae (L3) and L4, which have developed within the previous 30 days, and thus prevent disease caused by adult worms.

However, in recent years an increased number of lack of efficacy (LOE) cases have being reported, in which dogs develop mature heartworm infections despite receiving monthly prophylactic doses of macrocyclic lactones drugs. For example, Atkins et al, (*Veterinary Parasitology* 206 (2014) 106-113) recently reported that an increasing number of cases of dogs that tested heartworm antigen positive while receiving heartworm preventive medication which speculates that *Dirofilaria immitis* has developed selectional resistance to heartworm preventives (American Heartworm Society, 2010. Heartworm Preventive Resistance. Is it Possible, vol. 37. *Bulletin of the American Heartworm Society*, pp. 5). In recently reported studies, isolates of *D. immitis* with, in particular the JYD-34 *Dirofilaria immitis* strain, shows less than 100% susceptibility to heartworm preventive products in an induced heartworm infection model have been identified (Blagburn et al., Comparative efficacy of four commercially available heartworm preventive products against the JYD-34 laboratory strain of *Dirofilaria immitis*. In:

*Proceedings of the Triennial Heartworm Symposium,* vol.14, p. 39 (abstract); and Blagburn et al., Evidence of genetic selection following treatment of a heartworm-infected, microfilaremic dog with increasing dosages of ivermectin [abstract]. *Proc. Am. Assoc. Vet. Parasitol.* 58, 31).

A number of studies have shown some resistance of *D. immitis* larvae to macrocyclic lactones e.g. ivemectin, and milbemycin oxime. (*J. Vet. Intern. Med.* 2011; 25:61-64 and *Can. Vet. J.* 2011 December; 52(12): 1279-1280). It has recently been reported that a high frequency of a genotype marker has been correlated with potential macrocyclic resistance, for example some *D. immitis* strains having a single nucleotide polymorphism at sites 11 and 618 (GG-GG) of a gene encoding for P-glycoprotein have shown some resistance to ivermectin (*Topics in Companion Animal Medicine* Volume 26, Issue 4, Nov. 2011, Pages 186-192; *Veterinary Parasitology* 176 (2011) 374-381; and *Parasites & Vectors* 2014, 7:494). Also, recent reports indicate incomplete efficacy with normal prophylaxis regimens for treating MP3 strain of *D. immitis* with ivermectin, milbemycin oxime, or selamectin (http://www.delawarevalleyacademyvm.org/pdfs/may11/1Canine_Heartworm_2011.pdf; and *Veterinary Parasitology* 176 (2011) 189-194)". These reports suggest that the efficacy of most macrocyclic lactones may no longer be 100% against all *D. immitis* strains.

US 2011/0263489, U.S. Pat. No. 8,709,440, US 2014/0163056, US 2012/0295931, AU 2010249226 and AU2010101389 describes anthelmintic compositions in the form of a micellar solution, comprising at least two anthelmintic agents, wherein the anthelmintic agents for use treating by parasites resistant to one or more antiparasitic compounds.

U.S. Pat. No. 6,159,932 describes mixtures of avermectins, ivermectins and milbemycins in combination with cyclic depsipeptides, optionally in the presence of praziquantel or epsiprantel, for increasing the endoparasiticidal action in endoparasiticidal compositions.

US 2011/0046072 describes a delayed release solid pharmaceutical preparation comprising a least one pharmaceutically active ingredient which can include a depsipeptide and/or macrocyclic lactone and polyvinylpyrrolidone or a derivative thereof.

Notwithstanding the compositions comprising emodepside or macrocyclic lactones alone or in combination with other active agents described in the documents above, there is a need for veterinary compositions and methods with improved efficacy and spectrum of coverage to protect mammals against the constantly evolving resistance of parasites to present day treatments.

SUMMARY OF THE INVENTION

The present invention is directed to a combination of an effective amount of at least one cyclic depsipeptide and at least one macrocyclic lactone for the treatment or prophylaxis of parasites of mammals, in particular, cats, dogs, and humans with the aim of ridding these hosts of all the parasites commonly encountered, in particular parasites resistant to at least one anthelmintic macrocyclic lactone.

In certain embodiments invention also provides for effective and long lasting destruction of endoparasites, nematodes, such as filariae, hookworms, whipworms and roundworms of the digestive tract of mammals.

In an embodiment, the invention provides compositions and methods for the prevention of heartworm disease caused by a *Dirofilaria immitis* strain that is resistant to macrocyclic lactones. In a particular embodiment, the invention provides compositions and methods for the prevention of heartworm disease caused by a resistant strain of *Dirofilaria immitis*.

In particular this invention provides for a combination of at least one macrocyclic lactone derivative and at least one cyclic depsipeptide which exhibit additive or synergistic activity against parasites when compared to formulations which contain only macrocyclic lactone. The invention also provides for an easy method of treating parasitic infestations or for the prophylaxis of parasite infestations in mammals which may comprise administering to said mammal an effective amount of a combination composition according to the present invention.

These and other embodiments are disclosed or are apparent from and encompassed by, the following Detailed Description.

DETAILED DESCRIPTION OF THE INVENTION

Terms used herein will have their customary meaning in the art unless specified otherwise.

It is noted that the invention does not intend to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO ((35 U.S.C.) 112, first paragraph) or the EPO (Article 83 of the EPC), such that Applicants reserve the right and hereby disclose a disclaimer terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like.

Unless otherwise specifically noted or apparent by context, "active agent" or "active ingredient" or "therapeutic agent" as used in this specification, means an anthelmintic compound and/or cyclic depsipeptide of the invention.

Also, use of "a" or "an" are employed to describe elements and components of the invention. This is done merely for convenience and to give a general sense of the invention. This description should be read to include one or at least one and the singular also includes the plural unless it is obvious that it is meant otherwise.

The term "sequentially" or "sequential" as used herein refers to separate administration of each active agent in a sequential manner in either order, for example at an interval or intervals of minutes, hours, days or weeks, and if appropriate the active agents may be administered in a regular repeating cycle. If there is sequential administration, the delay in administering one of the active agents should not be such as to lose the benefit of the efficacious effect of the combination of the active agents. In all cases of "sequential" administration, the route of administration may be the same or different.

The term "concomitant" or "concomitantly" as used herein refer to the administration of at least two active agents to a mammal simultaneously. In all cases of "concomitant" administration, the route of administration may be the same or different.

The term "mammal" as used herein include, but are not limited to, cats, dogs and humans. It also includes an individual mammal in all stages of development, including embryonic and fetal stages.

The term "effective amount" as used herein means a concentration of the active agents in the composition sufficient to elicit the desired biological response to the target parasite(s) after administration of the composition to the animal, as measured by methods known in the art and/or described in the examples herein. In some embodiments, an "effective amount" of the active agents in the composition will provide an efficacy of at least 80%, or at least 85% compared to untreated controls. More typically, "an effective amount" of the active agents will provide an efficacy of at least 90%, at least 93%, at least 95% or at least 97% against the target parasite. In certain embodiments, including the the prevention of heartworm disease caused by a resistant strain of *Dirofilaria immitis*, the term "effective amount" may provide efficacy as high as 100%.

The term "treatment", "treating", and the like, as used herein, unless otherwise indicated, refers to eliminating, or ameliorating the parasitic infection, infestation, or condition. It also includes reducing the period of infection or incidence of symptoms of the parasitic infection, as well as references to "control" (e.g., kill, repel, expel, incapacitate, eliminate, alleviate, minimize, and eradicate).

The term "treatment or prophylaxis with the macrocyclic lactone alone" as used herein refers to treatment or prophylaxis with the macrocyclic lactone without treatment or prophylaxis with a cyclic depsipeptide.

The term "prophylaxis" or "prophylactic" or "preventative therapy", "prevention" or "protecting against" as referred to herein includes keeping the parasitic infection, or infestation, from occurring or to hinder, defend or protect from the occurance of a disease caused by the parasitic infection, as used herein, these terms also encompass, depending on the condition of the mammal, preventing the onset of a disorder or condition, or of symptoms associated with a disorder or condition, prior to affliction with said infection or infestation. For example, administration of the composition of the invention to a mammal so as to prevent heartworm disease caused by a resistant strain of *Dirofilaria immitis* by killing the third-stage larva (L3), as well as the young and maturing fourth-stage larva (L4) in the mammal, so that they do not mature into adult worms. Thus, these terms can refer to administration of the compounds of the present invention to a mammal that is not at the time of administration afflicted with the infection or infestation. As used herein, these terms also encompass preventing the recurrence of an infection or infestation or of symptoms associated therewith.

The terms "resistance", "resistant" and the like, as used herein, unless otherwise indicated, refers to the ability of a parasite to display a delayed, lessened and/or null response to treatment or prophylaxis with a macrocyclic lactone alone (i.e. without treatment with a cyclic depsipeptide) at the therapeutically recommended dosages, which would normally treat or protect against said parasites of the same species and stage. For example, after treatment with a macrocyclic lactone alone (i.e. without treatment with a cyclic depsipeptide), the parasitic load of a mammal infected with a macrocyclic lactone-resistant parasite (e.g. resistant *Dirofilaria immitis* strain) may be reduced to a lesser degree compared to the amount in parasitic load reduction exhibited by a mammal infected with a non-resistant parasitic strain. The term is used to include such separately identifiable forms of resistance as "full resistance", "immunity", "partial resistance", "hypersensitivity" and "tolerance". The term also includes parasitic-infected mammals unresponsive ("non-responders") to treatment with a macrocyclic lactone for parasitic infection, as well as parasitic-infected mammals who suffer a relapse following treatment with a macrocyclic lactone for parasitic infection ("responder-relapsers").

The term "pharmaceutically acceptable" as used herein means it is, within the scope of sound judgement in veterinary medicine, suitable for use in contact with the cells of a mammal without undue toxicity, irritation, allergic response and the like, and are commensurate with a reasonable benefit/risk ratio.

In a specific embodiment, the term "about" or "approximately" means within 20%, preferably within 10%, and more preferably within 5% of a given value or range.

In cases where compounds of the invention are sufficiently basic or acidic to form stable non-toxic acid or base salts, the compounds may be in the form of a pharmaceutically acceptable salt. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion Alkali metal (for example, sodium, potassium or lithium) or alkaline earth metal (for example calcium) salts of carboxylic acids can also be made.

In one embodiment, the compositions of the invention comprises an effective amount of:
  a) at least one cyclic depsipeptide;
  b) at least one macrocyclic lactone; and
  c) a pharmaceutically acceptable carrier;
for the treatment or prophylaxis of parasitic infection in a mammal wherein the parasite shows resistance to at least one macrocyclic lactone.

In another embodiment, the compositions of the invention further comprises praziquantel.

In another embodiment of the invention, the parasite is *Dirofilaria immitis*, more particularly a resistant *Dirofilaria immitis* strain containing single-nucleotide polymorphisms encoding a P-glycoprotein transporter, comprised of homozygous guanosine residues at sites 11 and 618 (GG-GG) of a gene encoding for P-glycoprotein ("GG-GG" genotype). In another embodiment of the invention, the parasite is a JYD 34 *Dirofilaria immitis* strain, MP3 *Dirofilaria immitis* strain or a combination thereof.

In another embodiment of the invention, the parasite is third-stage larvae (L3) or fourth-stage larvae (L4) of *Dirofilaria immitis* or a combination thereof.

In another embodiment of the invention, the cyclic depsipeptide is 24-membered cyclooctadepsipeptide.

In another embodiment of the invention, the cyclic depsipeptide is emodepside, PF1022A, a PF1022A derivative, or a combination thereof, more particularly, emodepside.

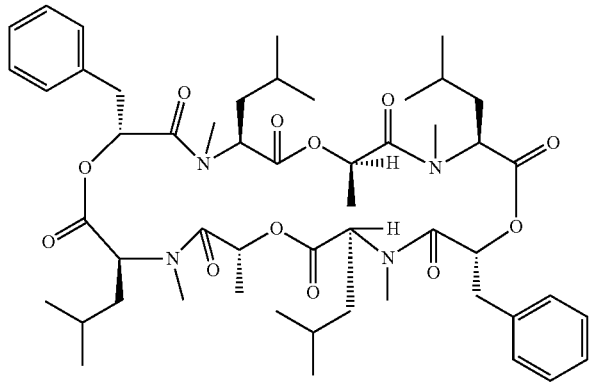

PF1022A

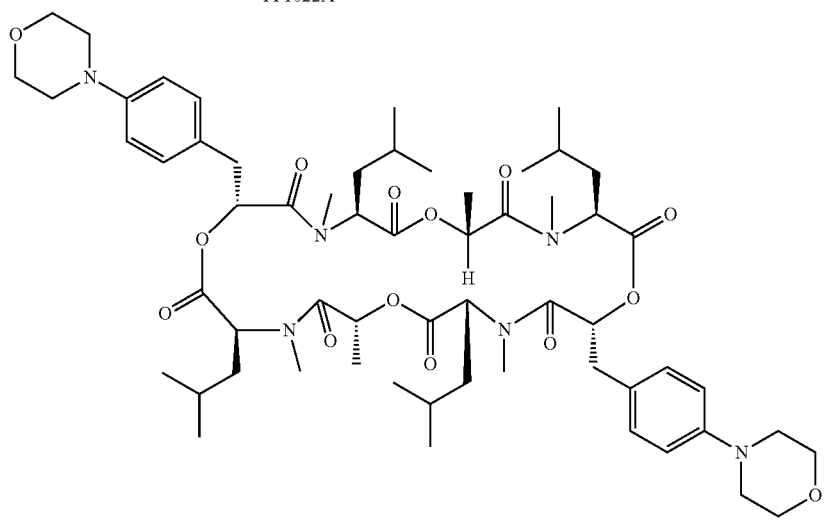

Emodepside

In another embodiment of the invention, the macrocyclic lactone of the composition is an avermectin, a milbemycin or a combination thereof, more particularly, a macrocyclic lactone selected from the group consisting of abamectin, dimadectin, doramectin, emamectin, eprinomectin, ivermectin, latidectin, lepimectin, selamectin, milbemycin oxime and moxidectin or a combination thereof, more particularly, ivermectin, eprinomectin, or moxidectin.

In another embodiment of the invention, the effective amount of macrocyclic lactone and cyclic depsipeptide is a synergistic effective amount.

In another embodiment of the invention the weight ratio of macrocyclic lactone to cyclic depsipeptide is about 1:500 to about 1:1000, about 1:833, 1:750 to about 1:1000, 1:500 to about 1:750, about 1:250 to about 1:500, about 1:417, about 1:100 to about 1:250, about 1:167, 1:150 to about 1:200, or about 1:50 to about 1:100. More preferably, the weight ratio of macrocyclic lactone to cyclic depsipeptide is about 1:100 to about 1:1000, or about 1:500 to about 1:1000.

In another embodiment of the invention, the weight ratio of macrocyclic lactone to praziquantel is about 1:50 to 1:5000, more preferably about 1:500 to about 1:5000, or about 1:3500 to about 1:5000.

In another embodiment of the invention, the veterinary composition is an oral formulation, injectable formulation, topical formulation, pour-on formulation, dermal formulation or sub-dermal formulations, preferably an oral formulation, a soft chewable composition or chewable tablet composition.

In another embodiment of the invention, the parasites controlled by the compositions and methods of the invention show resistance to at least one macrocyclic lactone selected from the group consisting of abamectin, dimadectin, doramectin, emamectin, eprinomectin, ivermectin, latidectin, lepimectin, selamectin, milbemycin-oxime, and moxidectin or a combination thereof, more particularly ivermectin.

In another embodiment of the invention, the mammal is selected from the group consisting of humans, dogs and cats more particularly dogs or cats.

Another embodiment of the invention is a veterinary composition comprising a synergistically effective amount of:
a) emodepside; and
b) ivermectin; and
a pharmaceutically acceptable carrier;
for the treatment or prevention of a parasitic infection, wherein the parasite is a resistant *Dirofilaria immitis* strain, more particularly the parasite is third-stage larvae (L3) or fourth-stage larvae (L4) of a resistant *Dirofilaria immitis* strain or a combination thereof.

In another embodiment of the invention, the veterinary composition further comprises praziquantel.

Another aspect of the invention is a method of treatment or prophylaxis of a parasitic infection in a mammal comprising administering to said mammal an effective amount of:
a) at least one cyclic depsipeptide; and
b) at least one macrocyclic lactone;
and a pharmaceutically acceptable carrier;
wherein the parasitic infection comprises a parasite that is resistant to at least one macrocyclic lactone.

Another embodiment of the invention is a method of treatment or prophylaxis of a parasitic infection wherein the parasitic infection comprises a parasite that is resistant to treatment or prophylaxis of the macrocyclic lactone when used alone.

Another embodiment of the invention is a method of treatment or prophylaxis of a parasitic infection in a mammal further comprising praziquantel or or epsiprantel or a combination thereof.

Another embodiment of the invention is a method of treatment or prophylaxis of a parasitic infection in a mammal, wherein the effective amount is a synergistic effective amount.

Another embodiment of the invention is a method of treatment or prophylaxis of a parasitic infection in a mammal, wherein the parasite is *Dirofilaria immitis*.

Another embodiment of the invention is a method of treatment or prophylaxis of a parasitic infection in a mammal wherein the parasite is a resistant *Dirofilaria immitis* strain.

Another embodiment of the invention is a method of treatment or prophylaxis of a parasitic infection in a mammal wherein the parasite is third-stage larvae (L3) or fourth-stage larvae (L4) of a resistant *Dirofilaria immitis* strain or a combination thereof.

Another embodiment of the invention is a method of treatment or prophylaxis of a parasitic infection in a mammal wherein the cyclic depsipeptide is 24-membered cyclooctadepsipeptide, more particularly, emodepside, PF1022A, a PF1022A derivative or a combination thereof. Examples of a PF1022A derivative include those cyclic depsipeptide compounds described in Table 2 of Ohyama, M., et al., Biosci. Biotechnol. Biochem., 75 (7), 1354-1363, 2011, which are incorporated herein in its entirety. More particularly, a PF1022A derivative comprises a cyclic depsipeptide compound selected from the group consisting of:

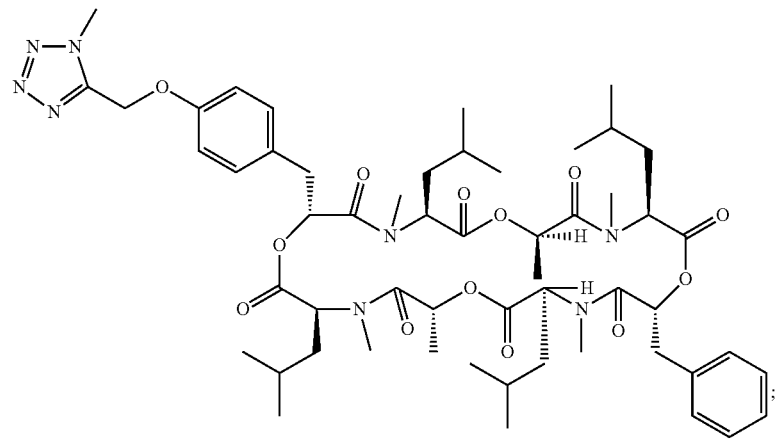

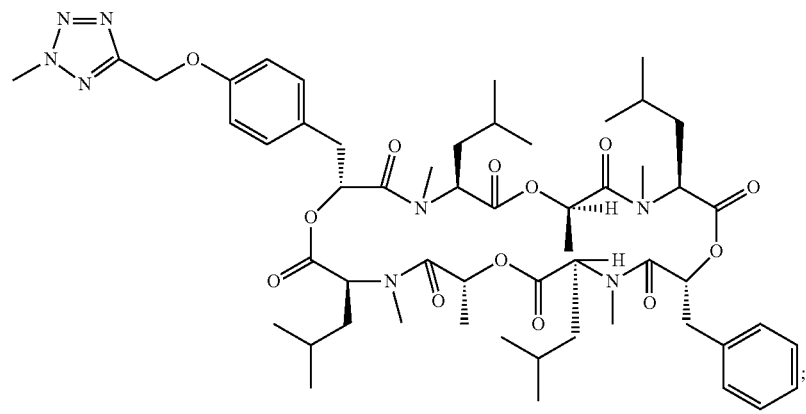

-continued
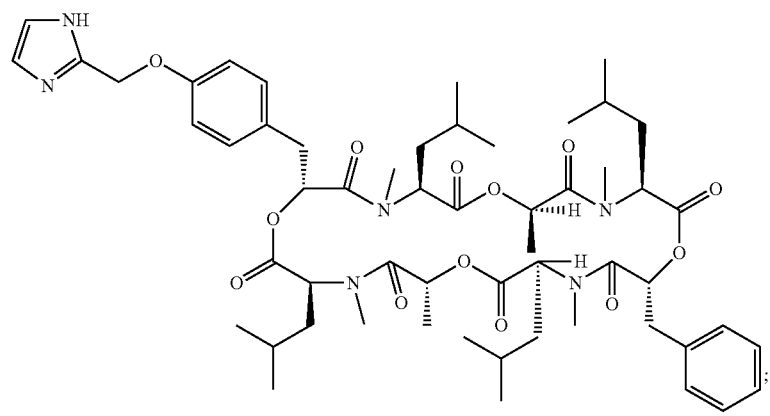
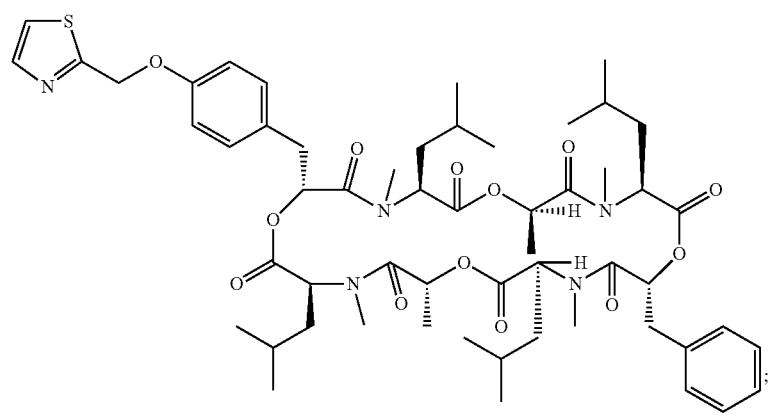
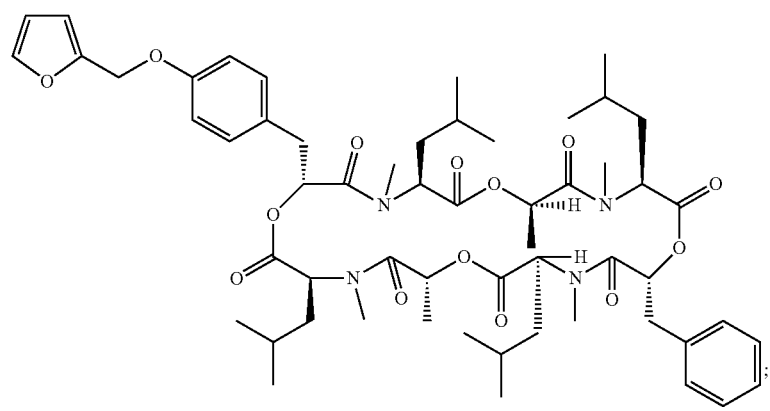
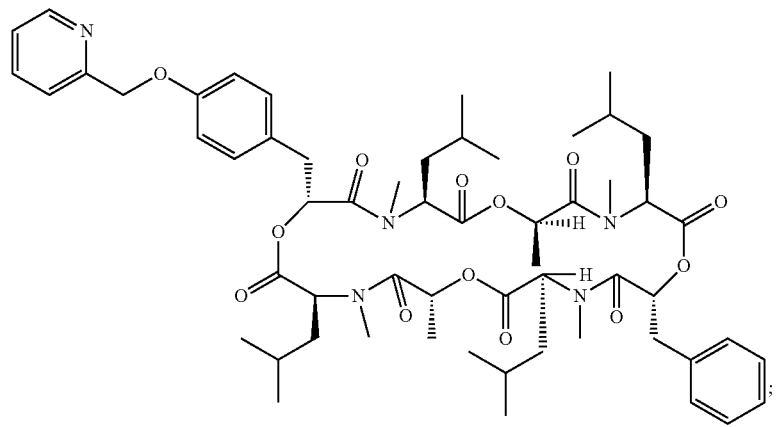

-continued
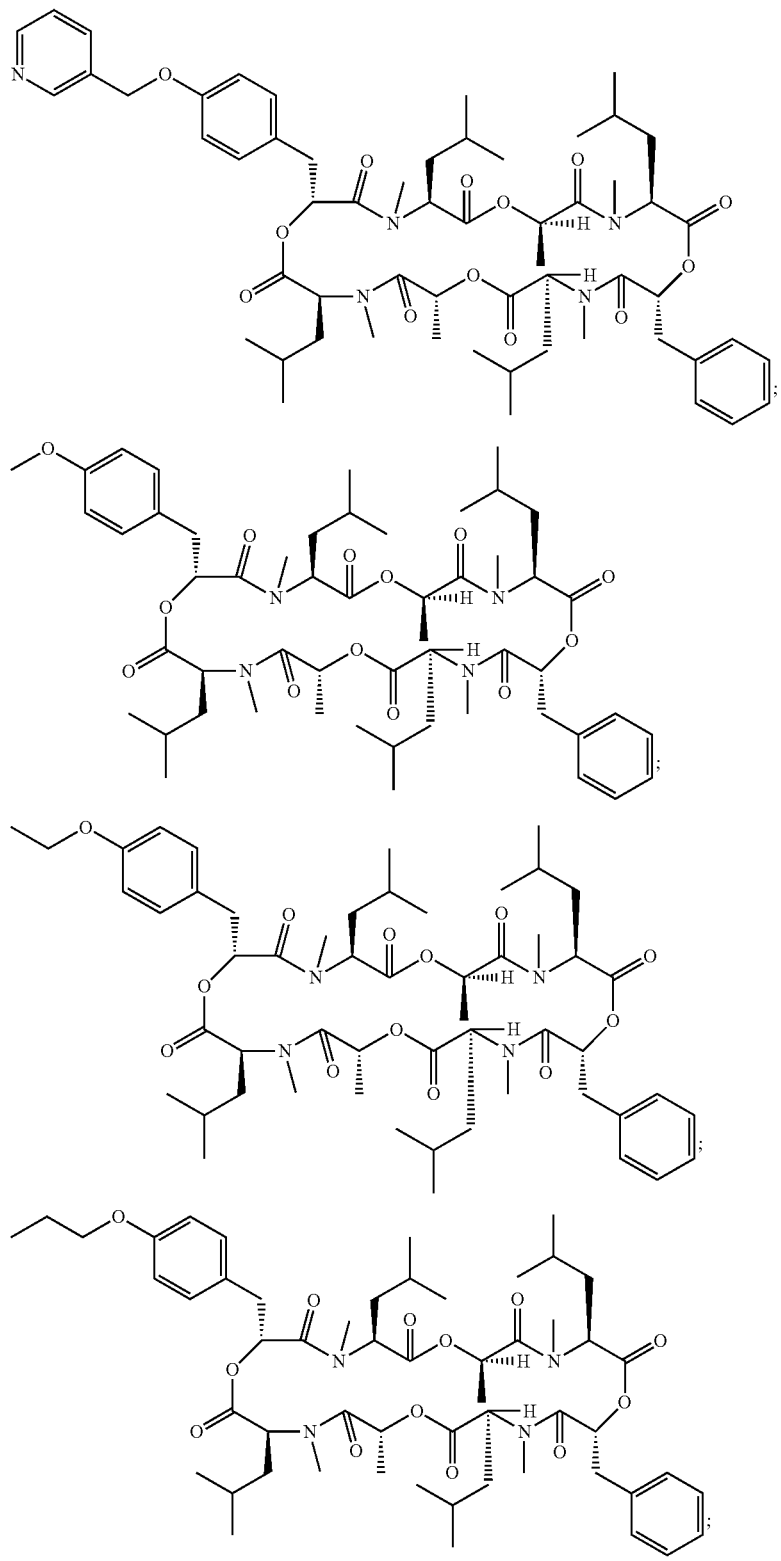

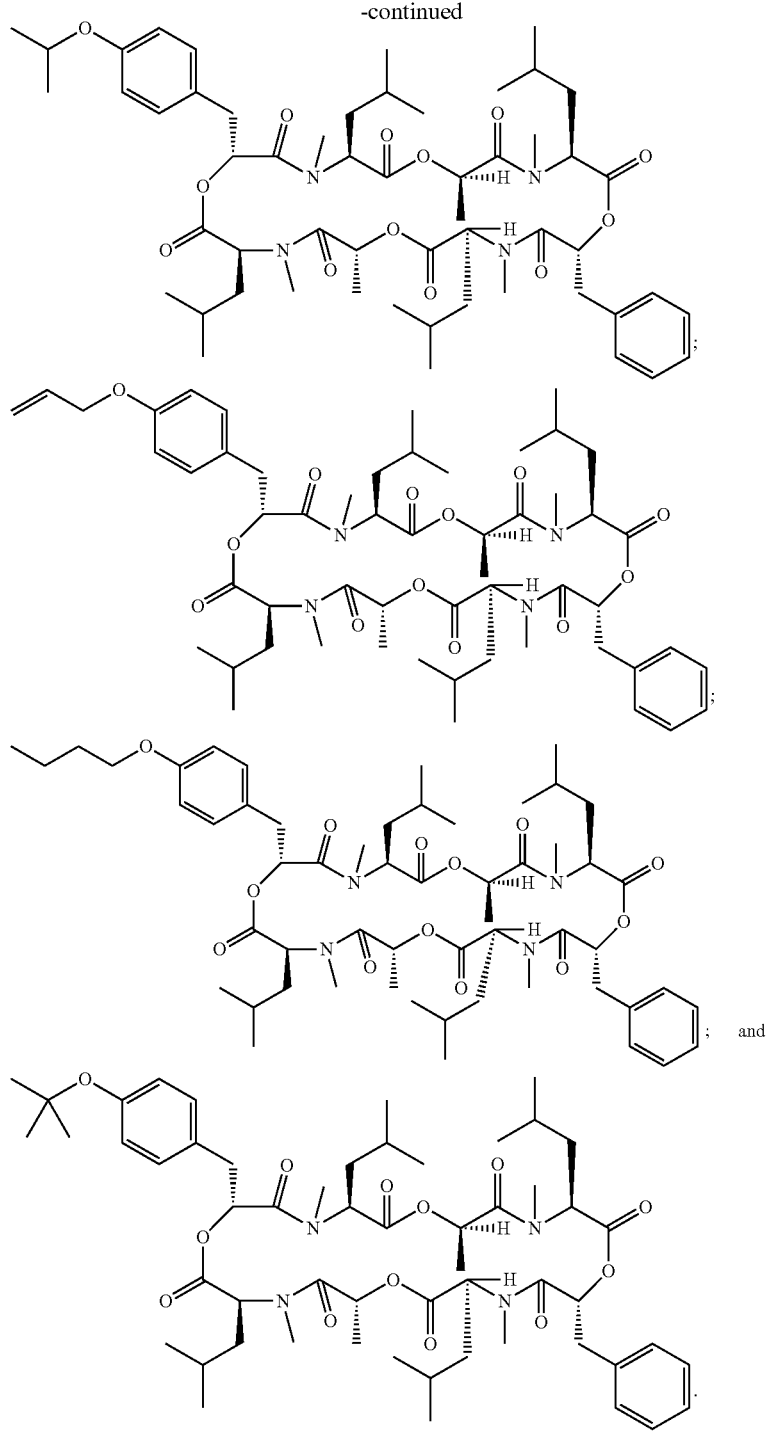

Another embodiment of the invention is a method of treatment or prophylaxis of a parasitic infection in a mammal wherein the cyclic depsipeptide is emodepside.

Another embodiment of the invention is a method of treatment or prophylaxis of a parasitic infection in a mammal wherein the macrocyclic lactone administered is an avermectin, a milbemycin or a combination thereof.

Another embodiment of the invention is a method of treatment or prophylaxis of a parasitic infection in a mammal wherein the macrocyclic lactone administered is selected from the group consisting of abamectin, dimadectin, doramectin, emamectin, eprinomectin, ivermectin, latidectin, lepimectin, selamectin, milbemycin oxime and moxidectin or a combination thereof.

In another embodiment of the invention, a method for the treatment or prophylaxis of a parasite infection in a mammal is provided comprising administering to the mammal an effective amount of a combination comprising a macrocyclic lactone selected from the group consisting of abamectin, dimadectin, doramectin, emamectin, eprinomectin, ivermectin, latidectin, lepimectin, selamectin, milbemycin oxime and moxidectin or a combination thereof; and a cyclic depsipeptide selected from emodepside, PF1022A, a PF1022A derivative or a combination thereof.

Another embodiment of the invention is a method of treatment or prophylaxis of a parasitic infection in a mammal wherein the macrocyclic lactone of the composition is ivermectin.

Another embodiment of the invention is a method of treatment or prophylaxis of a parasitic infection in a mammal which includes first treating the mammal with an adulticide such as thiacetarsamide sodium or melarsomine dihydrochloride, followed 3 to 6 weeks later by treatment with a) at least one cyclic depsipeptide; and b) at least one macrocyclic lactone; and a pharmaceutically acceptable carrier; wherein the parasitic infection comprises a parasite that is resistant to at least one macrocyclic lactone. Another embodiment of the invention is a method of treatment or prophylaxis of a parasitic infection in a mammal which further includes treatment with afoxolaner.

Another embodiment of the invention is a method of treatment or prophylaxis of a parasitic infection in a mammal, wherein the veterinary composition is an oral formulation, injectable formulation, topical formulation, pour-on formulation, dermal formulation or sub-dermal formulation, or more preferably an oral formulation with a soft chewable composition or a chewable tablet composition.

Another embodiment of the invention is a method of treatment or prophylaxis of a parasitic infection in a mammal wherein the parasites shows resistance to at least one macrocyclic lactone selected from the group consisting of abamectin, dimadectin, doramectin, emamectin, eprinomectin, ivermectin, latidectin, lepimectin, selamectin, milbemycin-oxime, and moxidectin or a combination thereof, more particularly ivermectin.

Another embodiment of the invention is a method of treatment or prophylaxis of a parasitic infection in a mammal wherein the mammal is selected from the group consisting of humans, dogs, and cats, more particularly dogs or cats.

Another embodiment of the invention is a method of treatment or prophylaxis of a parasitic infection in a mammal comprising administering to the mammal a synergistically effective amount of:
a) emodepside; and
b) ivermectin;
and a pharmaceutically acceptable carrier;
wherein the parasite is a resistant *Dirofilaria immitis* strain.

Another embodiment of the invention is a method of treatment or prophylaxis of a parasitic infection in a mammal which further comprises praziquantel.

Another embodiment of the invention is a method of treatment or prophylaxis of a parasitic infection in a mammal wherein the parasitic infection causes heartworm associated respiratory disease in the mammal.

Another embodiment of the invention is a method of treatment or prophylaxis of a parasitic infection in a mammal wherein the administration of the cyclic depsipeptide and macrocyclic lactone is concomitant.

Another embodiment of the invention is a method of treatment or prophylaxis of a parasitic infection in a mammal wherein the administration of the cyclic depsipeptide and macrocyclic lactone is sequential.

Another embodiment of the invention is a method of treatment or prophylaxis of a parasitic infection in a mammal which further comprises detecting the presence of the resistant parasitic strain in the mammal prior to administering said composition to the mammal.

Another embodiment of the invention is a method of treatment or prophylaxis of a parasitic infection in a mammal wherein the resistant parasitic strain is a resistant *Dirofilaria immitis* strain.

Another embodiment of the invention is a method of treatment or prophylaxis of a parasitic infection in a mammal wherein the administration is selected from the group consisting of enteral, oral, parenteral, topical, or transdermal.

A further embodiment of the invention is a kit, wherein the kit comprises:
i) at least one container;
ii) a synergistic effective amount of at least one cyclic depsipeptide and at least one macrocyclic lactone; and a pharmaceutically acceptable carrier; and
iii) instructions for use of the cyclic depsipeptide and macrocyclic lactone for treating or preventing a parasitic infection by a resistant *Dirofilaria immitis* strain.

A further embodiment of the invention is a kit which further comprises praziquantel.

A further embodiment of the invention is a kit wherein the cyclic depsipeptide and macrocyclic lactone are in the same container or separate containers.

A further embodiment of the invention is a kit wherein the container is selected from the group consisting of a blister pack, bottle, sachet, ampoule, syringe, pill popper device, drench gun, spray gun, pour-on device, pipette, dropper, spot-on device, or by any other container suitable for holding pesticides, or a combination thereof.

A further embodiment of the invention is a kit which further comprising an administration device for administering the cyclic depsipeptide and macrocyclic to a mammal.

A further embodiment of the invention is a kit wherein the administration device is selected from the group consisting of a syringe, pill popper device, drench bottle, drench gun, spray gun, transdermal patch, pour-on device, pipette dropper, spot-on device, ear-tag, collar, or by any other device suitable for administering drugs to mammals, or a combination thereof.

A further embodiment of the invention is a kit which further comprises a diagnostic tool for detecting the presence or absence of heartworm e.g. the *Dirofilaria immitis* strain.

A further embodiment of the invention is a kit wherein the diagnotistic tool is a detection assay which detects the presence or absence of nucleic acid primer pairs, combinations of nucleic acid primer pairs, nucleic acid arrays (e.g., diagnostic cards) containing nucleic acid primer pairs or combinations of nucleic acid primer pairs of heartworm e.g. the *Dirofilaria immitis* strain.

A further embodiment of the invention is a method of preventing parasitic infection in a mammal comprising administering a composition of the invention to said mammal, wherein the parasitic infection comprises at least one parasite resistant to at least one macrocyclic lactone.

A further embodiment of the invention is a method of preventing parasitic infection in a mammal by administering a composition of the invention to the mammal so as to kill the third-stage larva (L3), as well as the young and maturing fourth-stage larva (L4) of *Dirofilaria immitis* so that they do not mature into adult worms.

A further embodiment of the invention is a dosage, formulation, route of administration or dosing regimen as described for Treatment Group 4 or 5 in the Examples. Also provided are uses and methods comprising the compositions of the invention for the prevention or treatment of a parasitic infestation in birds or mammals or for in the manufacture of a medicament for the prevention or treatment of a parasitic infestation in birds or mammals.

Macrocyclic lactone anthelmintic compounds may be used for treating endo- and ectoparasite infections in mammals and birds. Compounds that belong to this class of macrocyclic lactones include, but are not limited to, the avermectin and milbemycin series of compounds. These compounds are potent antiparasitic agents against a wide range of internal and external parasites. Avermectins and milbemycins share the same common 16-membered macrocyclic lactone ring; however, milbemycins do not possess the disaccharide substituent on the 13-position of the lactone ring. In addition to treating parasitic insects, avermectins and milbemycins are used to treat endoparasites, e.g., round worm infections, in mammals.

The avermectins may be isolated from the fermentation broth of an avermectin producing strain of *Streptomyces avermifilis* and derivatives thereof. The production, isolation and structural determination of the avermectins are documented in Albers-Schonberg, et al., *J. Am. Chem. Soc.* 1981, 103, 4216-4221 and references cited therein. The description of the morphological characteristics of the culture is described in U.S. Pat. No. 4,310,519. Naturally occurring milbemycins are described in Aoki et al., U.S. Pat. No. 3,950,360, which is hereby incorporated by reference in its entirety, as well as in the various references cited in "The Merck Index" 12$^{th}$ ed., S. Budavari, Ed., Merck & Co., Inc. Whitehouse Station, N.J. (1996).

The avermectin and milbemycin series of compounds either are natural products or are semi-synthetic derivatives. The natural product avermectins are disclosed in U.S. Pat. No. 4,310,519, and the 22,23-dihydro avermectin compounds are disclosed in U.S. Pat. No. 4,199,569, both of which are hereby incorporated by reference in their entirety. The synthesis of avermectins has been documented (*J. Am. Chem. Soc.* 1989, 111, 2967; *J. Am. Chem. Soc.* 1986, 108, 2776) and research on deconjugation and epimerization of avermectin derivatives is also described in Hanessian, et al (*J. Am. Chem. Soc.* 1987, 109, 7063) and Fraser-Reid, et al (*J. Am. Chem. Soc.* 1987, 109, 933). For a general discussion of avermectins, which includes a discussion of their uses in humans and animals, see "Ivermectin and Abamectin," W. C. Campbell, ed., Springer-Verlag, New York (1989). Examples of avermectins include, but are not limited to, abamectin, dimadectin, doramectin, emamectin, eprinomectin, ivermectin, latidectin, lepimectin, and selamectin.

The milbemycins are the aglycone derivatives of the avermectins, such as those described, for example in U.S. Pat. Nos. 4,144,352; 4,791,134; and 6,653,342, all of which are hereby incorporated by reference in their entirety. Particularly important anthelmintics of this family include moxidectin, as described, for example in U.S. Pat. Nos. 7,348,417; and 4,916,154 (and references cited therein), which are hereby incorporated by reference in their entirety. Examples of milbemycins also include milbemectin, milbemycin D and nemadectin. Also included are the 5-oxo and 5-oxime derivatives of said avermectins and milbemycins, respectively.

The macrocyclic lactone compounds are known in the art and can easily be obtained commercially or through synthesis techniques known in the art. Reference is made to the widely available technical and commercial literature. For avermectins, such as ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

The avermectins and milbemycins demonstrate potent antiparasitic activity while being relatively non-toxic to most mammalian species. As a result, the avermectin/milbemycin family has been the focus of extensive chemical modification studies, which are outlined, for example, in U.S. Pat. Nos. 4,199,569; 4,285,963; 4,310,519; 4,423,209; 4,427,663; 4,457,920, 4,806,527; 4,831,016; 4,855,317; 4,859,657; 4,871,719; 4,873,224; 4,874,749; 4,895,837; 4,906,619, 4,920,148; 4,963,582; 4,973,711; 4,978,677; 5,015,630, 5,023,241, 5,030,622; 5,055,454; 5,055,596; 5,057,499; 5,077,308; 5,162,363; 5,169,839; 5,208,222; 5,244,879; 5,262,400; 5,637,703; 5,830,875; 7,250,402; and EP 0 212 867; 0 237 339; 0 241 146; 0 214 731; 0 194 125; and 0 170 006, all of which are hereby incorporated by reference in their entirety. Further modifications of members of the avermectin family are outlined, for example, in U.S. patent application Ser. Nos. 10/488,225; 10/498,858; 10/513,247; 10/539,274; 10/543,637; 10/543,638; 10/543, 643, 10/544,274; 10/544,281; 10/560,390; 10/568,715; 10/599,671; 11/317,932; 11/319,686; and 11/319,687, all of which are hereby incorporated by reference in their entirety. Chemical modifications have also been induced via spiking the fermentation broth with acids, which are subsequently incorporated at the C-25 position of the avermectins (EP 0 214 731, and *Arch. Biochem. Biophys* 1989, 269, 544-547). All of these documents and references cited therein, as well as the references cited herein, are expressly incorporated by reference.

Notwithstanding the excellent progress in antiparasitic research, concerns remain with respect to increasingly common reports of resistance among veterinary parasites (*Parasitology* 2005, 131, S179-190). Thus, there remains an ongoing need for novel compositions and treatments in veterinary medicine. It is an object of this invention to provide novel formulations comprising cyclic depsipeptides and macrocyclic lactones, as well as methods of treatment using such compounds. That the invention performs as herein described is surprising, unexpected and nonobvious.

While the macrocyclic lactones are well known antiparasitic compounds, there remains an ongoing need to combat the constantly evolving resistance of parasites. To this end, we have found that a combination of macrocyclic lactones and cyclic depsipeptides are effective in treating certain resistant parasites, in particular *Dirofilaria immitis*, more particularly JYD-34 *Dirofilaria immitis* strain.

Cyclic depsipeptides, in particular cyclooctadepsipeptides such as PF1022A or emodepside, which act at the neuromuscular junction by stimulating presynaptic receptors belonging to the secretin receptor family resulting in the paralysis and death of parasites. Cyclic depsipeptides of the invention include compounds consisting of amino acids and hydroxycarboxylic acids as ring structural units and 8 to 30 ring atoms, such as PF 1022A, emodepside, and others described in, U.S. Pat. No. 5,380,745, US 2003/0143254A1, US005571793A, U.S. Pat. Nos. 5,514,773, 5,821,222, 5,646,244, 5,874,530, 6,159,932, 5,856,436, 6,033,879, 5,763,221, 6,329,338, 6,355,615, 6,265,537, 6,043,058, 6,146,853, 6,630,569, 7,285,404, 7,109,018, 6,916,641, 6,828,300, 6,900,176, 7,432,102, 7,763,583, US2012302496, WO12/028556, US2015166608, U.S. Pat. Nos. 5,777,075, 6,369,028, 5,116,815, 5,747,448, 5,116,815, and 5,380,745, which are incorporated herein by reference for all relevant purposes.

The compositions of the invention may also include paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J Antibiotics* 1990, 43, 1380, and *J Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. Nos. 5,703,078 and 5,750,695, all of which are hereby incorporated by reference in their entirety. The compositions of the invention may also include at least one additional systemically-acting active agents described herein including, but not limited to, one or more isoxazoline active agents, or anthelmintics of other classes including one or more amino acetonitrile active agents, one or more aryloazol-2-yl cyanoethylamino active agents, or a combination thereof.

The compositions of the invention may also include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance,*" in Comprehensive Molecular Insect Science, vol. 6, pp. 137-173, 2005) or a semisynthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In some embodiments, the compositions may contain a combination of two or more spinosyn and/or spinosoid active agents. For example, in one embodiment, the compositions may include spinosad, which is a combination of spinosyn A and spinosyn D. Other combinations are also contemplated. In another embodiment, the compositions may include a spinosyn and/or a spinosoid active agent, or a combination thereof, in combination with one or more additional systemically-acting active agents described herein including, but not limited to, one or more isoxazoline active agents, one or more macrocyclic lactone active agents, one or more benzimidazole agents including thiabendazole, oxibendazole, mebendazole, fenbendazole, oxfendazole, albendazole, triclabendazole and febantel, or anthelmintics of other classes including levamisole, pyrantel, morantel, praziquantel, closantel, clorsulon, one or more amino acetonitrile active agents, one or more insect growth regulators, one or more neonicotinoid active agents or an aryloazol-2-yl cyanoethylamino active agent, or a combination thereof.

The phenylpyrazoles as a class are known in the art and are described, for example in U.S. Pat. Nos. 5,885,607; 6,010,710; 6,083,519; 6,096,329; 6,395,765, 6,867,229, EP-A-295,217, EP-A-352,944 as well as in U.S. Pat. Nos. 5,576,429; 5,122,530, U.S. patent application Ser. No. 11/825,050, and EP 295 177, the disclosures of which, as well as the references cited herein, are incorporated by reference. This class of insecticides is known to possess excellent activity against insects such as ticks and fleas, and one of these compounds, 1-[2,6-Cl$_2$-4-CF$_3$ phenyl]-3-CN-4-[SO—CF$_3$]-5-NH$_2$pyrazole, or fipronil, may be included in the compositions and methods of the invention in certain embodiments, The combinations according to the invention, comprising an effective amount of at least one cyclic depsipeptide and at least one macrocyclic lactone exhibit an unexpected synergistic effect in treating parasites showing resistance to at least one anthelmintic macrocyclic lactone.

The combinations according to the invention, comprising an effective amount of at least one cyclic depsipeptide and at least one macrocyclic lactone exhibit an unexpected synergistic effect in treating parasites showing resistance to Ivermectin.

The combinations according to the invention, comprising an effective amount of at least one cyclic depsipeptide, for example emodepside, and at least one macrocyclic lactone, for example ivermectin, exhibit an unexpected synergistic effect in preventing third-stage larvae (L3) as well as fourth-stage larvae (L4) of a resistant *Dirofilaria immitis* strain, from maturing into adult worms.

Synergism has been described as "the cooperative action of two components (e.g., component (a) and component (b)) in a mixture, such that the total effect is greater or more prolonged than the sum of the effects of the two (or more) taken independently" (see P. M. L. Tames, *Neth. J Plant Pathology* 1964, 70, 73-80). Mixtures containing an effective amount of at least one cyclic depsipeptide and at least one macrocyclic lactone are found to exhibit synergistic effects against certain important pests. Successful combinations of an effective amount of at least one cyclic depsipeptide and at least one macrocyclic lactone provides improved and even synergistic effect over mono-therapy, i.e. pharmaceutical treatment limited to one drug e.g. macrocyclic lactones or cyclic depsipeptides, particularly against resistant strains of parasites such as a resistant strain of *Dirofilaria immitis*.

If the macrocyclic lactone and cyclic depsipeptide in the combinations according to the invention are present in certain weight ratios, the synergistic effect is particularly pronounced. However, the weight ratios of the macrocyclic lactone and cyclic depsipeptide in the combinations can be varied within a relatively wide range. In general, the combinations according to the invention comprise macrocyclic lactone and cyclic depsipeptide in the preferred ratios given.

An additive or synergistic effect may be attained when the macrocyclic lactone and cyclic depsipeptide are: (1) co-formulated and administered or delivered simultaneously in a combined, unit dosage formulation; (2) delivered by alternation or in parallel as separate formulations; or (3) by some other regimen. When delivered in alternation therapy, an additive or synergistic effect may be attained when the macrocyclic lactone and cyclic depsipeptide are administered or delivered sequentially, e.g., by seperate oral administrations in different unit dosage forms. In general, during alternation therapy, an effective dosage of each active ingredient is administered sequentially, i.e., serially, whereas in combination therapy, effective dosages of two or more active ingredients are administered together.

The composition of the invention may also be in a variety of forms which include, but are not limited to, oral formulations, injectable formulations, and topical, pour-on, dermal or subdermal formulations. The formulations are intended to be administered to a mammal. Examples of mammals include but are not limited to humans, dogs, cats and other livestock or domestic mammals. The composition of the invention may be in a form suitable for oral use, for example, as baits (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range selected from the group consisting of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment of the glycol derivatives, the glycol may be selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include but are not limited to those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and polyoxamers (e.g., Pluronic L 81); an absorbent selected from the group consisting of magnesium carbonate, calcium carbonate, starch, and cellulose and its derivatives; and a colorant selected from the group consisting of titanium dioxide iron oxide, and FD&C Blue #1 Aluminum Lake.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive composition including a spot-on, spray-on or pour-on composition, may allow for the inventive composition to be absorbed through the skin to achieve systemic levels, distributed through the sebaceous glands or on the surface of the skin achieving levels throughout the haircoat. When the compound is distributed through the sebaceous glands, they may act as a reservoir, whereby there may be a long-lasting effect (up to several months) effect. Spot-on formulations are typically applied in a localized region which refers to an area other than the entire mammal. In one embodiment of a localized region, the location may be between the shoulders. In another embodiment of a localized region it may be a stripe, e.g. a stripe from head to tail of the mammal Pour-on formulations are described in U.S. Pat. No. 6,010,710, also incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that may be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the compounds of the invention and their solubilities in this solvent. It will be sought to have the lowest possible volume. The vehicle makes up the difference to 100%.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor, an organic solvent and an organic co-solvent.

In one embodiment of the amount of crystallization inhibitor, the crystallization inhibitor may be present in a proportion of about 1 to about 30% (w/v) or about about 5 to about 15%. In other embodiments, the amount of crystallization inhibitor in the inventive formulations may be about 1% to about 20%, about 1% to about 15%, or about 1% to about 10% (w/w).

In some embodiments, the organic solvent may have a dielectric constant of between about 10 and 35 or between about 20 and 30, the content of this organic solvent in the overall composition representing the complement to 100% of the composition.

In some embodiments, the organic co-solvent may have a boiling point of below about 100° C., or below about 80° C. In other embodiments, the organic co-solvent may have a boiling point of below about 250° C., below about 230° C., below about 210° C. or below about 200° C. In other embodiments, the organic co-solvent may have a dielectric constant of between about 10 and 40 or between about 20 and 30. In some embodiments, the co-solvent may be present in the composition in a organic co-solvent/organic solvent weight/weight (W/W) ratio of between about 1/15 and 1/2. The solvent may act as to improve solubility or as a drying promoter, and is miscible with water and/or with the organic solvent.

The formulation may also comprise an antioxidizing agent intended to inhibit oxidation in air, this agent being present in a proportion selected from a range consisting of about 0.005 to about 1% (w/v) and about 0.01 to about 0.05%.

The type of crystallization inhibitor used in the inventive formulations is not limited as long as it functions to inhibit crystallization or precipitation of the active or inactive agents from the formulation. Crystallization inhibitors which are useful for the invention may include but are not limited to:

(a) polyvinylpyrrolidone, polyvinyl alcohols, copolymers of vinyl acetate and of vinylpyrrolidone, polyethylene glycols, benzyl alcohol, N-methylpyrrolidone, mannitol, glycerol, sorbitol or polyoxyethylenated esters of sorbitan; lecithin or sodium carboxymethylcellulose; or acrylic derivatives, such as methacrylates and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur; that is to say without a tendency towards sticking or towards a sticky appearance, despite the high concentration of active material.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied may be of the order of about 0.3 to about 1 ml. In one embodiment for the volume, the volume may be on the order of about 0.5 ml, for cats and on the order of about 0.3 to about 3 ml for dogs, depending on the weight of the mammal In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the mammal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monoethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle may optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the mammal. These formulations will vary with regard to the weight of the therapeutic agent in the combination depending on the species of host mammal to be treated, the severity and type of infection and the body weight of the host.

Dosage forms may contain from about 0.5 mg to about 5 g of each active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, each active agent may be present in the formulation at a concentration of about 0.05 to 10% weight/volume. In another embodiment of the invention, the active agent may be present in the formulation as a concentration from about 0.1 to 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

In one embodiment of the invention, administration of the active agents may be performed at any of various intervals (e.g., daily, weekly, or monthly) and the dosage, frequency, and mode of administration of each agent can be determined individually. For example, administration of cyclic depsipeptide and macrocyclic lactone; may be hourly, daily, weekly, monthly, yearly, or a single event. In a preferred embodiment the administration of cyclic depsipeptide and macrocyclic lactone is monthly. In addition, administration can have a duration of from six months to one year or more.

It will be appreciated in another embodiment of the invention, the active agents of the combination may be administered concomitantly, either in the same or different pharmaceutical formulation or sequentially. In another embodiment of the invention, the active composition may be administered via a drench, and may be administered either topically or orally. Drench formulations are those in which the liquid containing the compositions of the invention is administered to the mouth or throat of the mammal, or poured onto the skin or coat of the mammal.

The invention is also directed toward a method of treating a mammal against ectoparasitic infection by administering an ectoparasiticidally effective amount of the composition of the invention. Mammals which can be treated include but are not limited to humans, cats, and dogs.

In one embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheylefiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like). In yet another embodiment for the treatment against ectoparasites, the ectoparasite is a flea and/or tick.

Additional examples of ectoparasites include but are not limited to the tick genus *Boophilus*, especially those of the species microplus (cattle tick), decoloratus and annulatus; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

The compositions of the invention can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*.

In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example *Acarus siro, Aceria sheldoni, Aculops* spp., *Aculus* spp., *Amblyomma* spp., *Argas* spp., *Boophilus* spp., *Brevipalpus* spp., *Bryobia praefiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) from the order of Coleoptera, for example, *Acanthoscelides obtectus, Adoretus* spp., *Agelasfica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., Dicrocoelium spp, Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebormi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Dicono-*

*coris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the invention, the compounds and compositions of the invention can be applied against a single pest or combinations thereof.

Additional pharmaceutical, pesticidal or veterinarily active ingredients, which include, but are not limited to, parasiticidals including acaricides, anthelmintics, endectocides and insecticides, may also be added to the compositions of the invention. Anti-parasitic agents may include both ectoparasiticisal and endoparasiticidal agents. Veterinary pharmaceutical agents are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, afoxolaner, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidie, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate/DSS, dolasetron mesylate, domperidone, dopamine HCl, doramectin, doxapram HCl, doxepin HCl, doxorubicin HCl, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCl, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (oxyglobin®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinopril, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide HCl, metoprolol, metronidaxole, mexiletine HCl, mibolerlone, midazolam HCl milbemycin oxime, mineral oil, minocycline HCl, misoprostol, mitotane, mitoxantrone HCl, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone HCl, oxytretracycline, oxytocin, pamidronate disodium, pancreplipase, pancuronium bromide, paromomycin sulfate, parozetine HCl, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine HCl, pheylbutazone, phenylephrine HCL, phenypropanolamine HCl, phenytoin sodium, pheromones, parenteral phosphate, phytonadione/vitamin K-1, pimobendan, piperazine, pirlimycin HCL, piroxicam, polysulfated glycosaminoglycan, ponazuril, potassium chloride, pralidoxime chloride, praziquantel, prazosin HCl, prednisolone/prednisone, primidone, procainamide HCl, procarbazine HCl, prochlorperazine, propantheline bromide, *Propionibacterium acnes* injection, propofol, propranolol HCl, protamine sulfate, pseudoephedrine HCl, psyllium hydrophilic mucilloid, pyrantel pamoate, pyridostigmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCL/l-deprenyl, sertraline HCl, sevelamer HCl, sevoflurane, silymarin/milk thistle, sodium bicarbonate, sodium polystyrene sulfonate, sodium stibogluconate, sodium sulfate, sodum thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thiotepa, thyrotropin, tiamulin, ticarcilin disodium, tiletamine HCl/zolazepam HCl, tilmocsin, tiopronin, tobramycin sulfate, tocainide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zafirlukast, zidovudine (AZT), zinc acetate/zinc sulfate, zonisamide and mixtures thereof.

In one embodiment of the invention, arylpyrazole compounds may be added to the compositions of the invention. Arylpyrazoles may include but are not limited to those described in U.S. Pat. Nos. 6,001,384; 6,010,710; 6,083,519; 6,096,329; 6,174,540; 6,685,954 and 6,998,131, all of which are hereby incorporated by reference in their entirety,—each assigned to Merial, Ltd., Duluth, Ga.).

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment of the invention, the class of acaricides or insecticides known as insect growth regulators (IGRs) may also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356; 3,818,047; 4,225,598; 4,798,837; 4,751,225, EP 0 179 022 or U. K. 2 140 010 as well as U.S. Pat. Nos. 6,096,329 and 6,685,954, all of which are hereby incorporated by reference in their entirety, (both assigned to Merial Ltd., Duluth, Ga.). Examples of IGRs suitable for use may include but are not limited to methoprene, pyriproxyfen, hydroprene, cyromazine, fluazuron, lufenuron, novaluron, pyrethroids, formamidines and 1-(2, 6-difluorobenzoyl)-3-(2-fluoro-4-(trifluoromethyl)phenylurea.

An anthelmintic agent that may be combined with the compositions of the invention may be a benzenedisulfonamide compound, which includes but is not limited to clorsulon; or a cestodal agent, which includes but is not limited to praziquantel, pyrantel or morantel A parasiticidal agent that may be combined with the compositions of the invention may be a biologically active peptide or protein including, but not limited to, depsipeptides, which act at the neuromuscular junction by stimulating pre synaptic receptors belonging to the secretin receptor family resulting in the paralysis and death of parasites. In one embodiment the depsipeptide may be emodepside.

An insecticidal agent that may be combined with the compositions of the invention may be a spinosyn (e.g. spinosad) or a substituted pyridylmethyl derivative compound such as imidacloprid. Agents of this class are described above, and for example, in U.S. Pat. No. 4,742, 060 or in EP 0 892 060, both of which are hereby incorporated by reference in their entirety. It would be well within the skill level of the practitioner to decide which individual compound may be used in the inventive formulation to treat a particular infection of an insect. For endoparasites, parasiticides which may be combined include but are not limited to pyrantel, morantel, the benzimidazoles (including albendazole, cambendazole, thiabendazole, fenbendazole, febantel, oxfendazole, oxibendazole, triclabendazole mebendazole and netobimin), levamisole, closantel, rafoxanide, nitroxynil, disophenol and paraherquamide. For ectoparasites, insecticides which may be combined also include but are not limited to pyrethoids, organophosphates and neonicotinoids such as imidacloprid, as well as compounds such as metaflumizone, amitraz and ryanodine receptor antagonists.

Where appropriate, the anthelmintic, parasiticidal and insecticial agent may also be selected from the group of compounds described above as suitable for agrochemical use.

In general, the additional pesticidal agent may be included in a dose of between about 0.1 µg and about 10 mg. In one embodiment of the invention, the additional pesticidal agent may be included in a dose of between about 1 µg and about 10 mg. In another embodiment of the invention, the additional pesticidal agent may be included in a dose of about 5 to about 200 µg/kg of weight of mammal. In yet another embodiment of the invention, the additional pesticidal agent may be included in a dose between about 0.1 to about 10 mg/kg of weight of mammal. In still another embodiment of the invention, the additional pesticidal agent may be included in a dose between about 0.5 to 50 mg/kg.

A further embodiment of the invention includes a diagnostic tool for testing the presence or absence of a parasitic strain. For example, US20070042354, US20110223599, 20030129680, 20110223599 discloses systems, methods, and compositions for identifying a subject infected with a parasite.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. This invention includes all modifications and equivalents of the subject matter recited in the aspects or claims presented herein to the maximum extent permitted by applicable law.

Certain aspects of the invention are further described by the following Examples:

EXAMPLES

The following examples are provided to illustrate certain embodiments of the invention and are not to be construed in any way as limiting the scope of the invention.

Study of the Efficacy of Ivermectin and Emodepside, Separately and in Combination, Against *Dirofilaria immitis*:

Ten male and ten female healthy Beagle dogs, 5.2 to 6.2 months of age, weighing 7.3 to 10.3 kg were studied.

Dogs were tested for microfilaria and heartworm antigen and received a full physical examination prior to inclusion in the study. Each dog was inoculated with 50 infective third-stage *D. immitis* larvae on Day-7 (JYD-34 isolate). Antigen testing performed on blood collected on Day 111 confirmed that animals had not been exposed to *D. immitis* prior to the induced infection.

Four blocks of five dogs each were formed based on descending Day -2 body weights within sex. Within blocks, dogs were randomly allocated to one of five treatment groups by lottery and treated orally five times at monthly intervals with an oral solution of ivermectin, Profender® (emodepside+praziquantel) tablets or a combination of an ivermectin solution and Profender® tablets at monthly dosing intervals for according to the following table:

TABLE 1

| Treatment Group | Investigational Material | Dose | Efficacy |
| --- | --- | --- | --- |
| 1 | Untreated Control | NA | NA |
| 2 | ivermectin oral solution | 6 mcg/kg (0.15 mL/kg) | Less than 50% |
| 3 | Profender ® Tablet(s): emodepside + praziquantel | 1 mg/kg 5 mg/kg | Less than 50% |
| 4 | ivermectin oral solution and Profender ® Tablet(s): emodepside + praziquantel | 6 mcg/kg (0.15 mL/kg) and 1 mg/kg 5 mg/kg | 81% |
| 5 | ivermectin oral solution and Profender ® Tablet(s): emodepside + praziquantel | 6 mcg/kg (0.15 mL/kg) and 5 mg/kg 25 mg/kg | 100% |

All animals were humanely euthanized on Day 160 and a necropsy was performed for parasite recovery and live *D. immitis* counts for individual dogs. The percent efficacies by treatment group are listed in Table 1.

In this study, ivermectin solution (6 mcg/kg), administered orally in combination with Profender® tablets (5 mg/kg emodepside plus 25 mg/kg praziquantel) for five months, provided 100% efficacy against induced infections of the JYD-34 isolate of *Dirofilaria immitis*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the treatment or prophylaxis of a *Dirofilaria immitis* parasitic infection in a canine by a *Dirofilaria immitis* strain that is resistant to treatment or prophylaxis with a macrocyclic lactone alone, wherein the *Dirofilaria immitis* parasitic infection is third-stage larvae (L3) or fourth-stage larvae (L4) or a combination thereof, said method comprising
orally administering once monthly to said canine a combination of:
a) at least 5 mg/kg of at least one cyclic depsipeptide; and
b) at least 6 mcg/kg of at least one avermectin;
and a pharmaceutically acceptable carrier; wherein
a) and b), with the pharmaceutically acceptable carrier, are administered concomitantly; and
the administering results in the 100% efficacy treatment or prophylaxis against infection by the *Dirofilaria immitis* strain that is resistant to treatment or prophylaxis with the macrocyclic lactone alone.

2. The method according to claim 1, further comprising administering praziquantel or epsiprantel, or a combination thereof.

3. The method according to claim 1, wherein the cyclic depsipeptide is 24-membered cyclooctadepsipeptide.

4. The method according to claim 1, wherein the cyclic depsipeptide is emodepside, PF1022A, a PF1022A derivative or a combination thereof.

5. The method according to claim 1, wherein the cyclic depsipeptide is emodepside.

6. The method according to claim 1, wherein
the avermectin administered is selected from the group consisting of avermectin, abamectin, dimadectin, doramectin, emamectin, eprinomectin, ivermectin, latidectin, lepimectin, and selamectin, or a combination thereof; and
the cyclic depsipeptide is selected from the group consisting of emodepside, PF1022A, and a PF1022A derivative, or a combination thereof.

7. The method according to claim 1, wherein the avermectin administered is selected from the group consisting of avermectin, abamectin, dimadectin, doramectin, emamectin, eprinomectin, ivermectin, latidectin, lepimectin, and selamectin, or a combination thereof.

8. The method according to claim 1, wherein the avermectin of the composition is ivermectin.

9. The method according to claim 8, wherein the cyclic depsipeptide is emodepside.

10. The method according to claim 1, wherein the macrocyclic lactone, to which the *Dirofilaria immitis* strain is resistant, is selected from the group consisting of abamectin, dimadectin, doramectin, emamectin, eprinomectin, ivermectin, latidectin, lepimectin, selamectin, milbemycin-oxime, and moxidectin, or a combination thereof.

11. The method according to claim 1, wherein the macrocyclic lactone, to which the *Dirofilaria immitis* strain is resistant, is ivermectin.

12. The method according to claim 1, wherein the administering is performed five times.

13. The method according to claim 1, wherein
the cyclic depsipeptide is emodepside or PF1022A; and
the macrocyclic lactone is selected from the group consisting of abamectin, dimadectin, doramectin, emamectin, eprinomectin, ivermectin, latidectin, lepimectin, and selamectin.

* * * * *